United States Patent
Bonisch et al.

(10) Patent No.: US 9,494,564 B2
(45) Date of Patent: Nov. 15, 2016

(54) TUNNEL MONITORING SENSOR

(71) Applicant: SICK AG, Waldkirch/Breisgau (DE)

(72) Inventors: Andreas Bonisch, Gundelfingen (DE); Jurgen Convent, Waldkirch (DE)

(73) Assignee: SICK AG, Waldkirch/Breisgau (DE)

( * ) Notice: Subject to any disclaimer, the term of this patent is extended or adjusted under 35 U.S.C. 154(b) by 0 days.

(21) Appl. No.: 14/105,502

(22) Filed: Dec. 13, 2013

(65) Prior Publication Data
US 2014/0174153 A1    Jun. 26, 2014

(30) Foreign Application Priority Data
Dec. 21, 2012   (EP) .................................. 12198882

(51) Int. Cl.
G01N 21/53    (2006.01)
G01N 33/00    (2006.01)

(52) U.S. Cl.
CPC ........ G01N 33/0009 (2013.01); G01N 21/538 (2013.01); G01N 33/007 (2013.01)

(58) Field of Classification Search
CPC ........................ G01N 33/0009; G01N 21/538
See application file for complete search history.

(56) References Cited

U.S. PATENT DOCUMENTS

| | | | |
|---|---|---|---|
| 4,362,387 A * | 12/1982 | Clark | 356/338 |
| 6,724,917 B1 | 4/2004 | Ohashi et al. | |
| 6,865,448 B1 * | 3/2005 | Rotman et al. | 700/275 |
| 7,302,805 B2 | 12/2007 | Tille et al. | |
| 2001/0040509 A1 * | 11/2001 | Dungan | 340/632 |
| 2013/0137356 A1 * | 5/2013 | Pavetic et al. | 454/167 |

FOREIGN PATENT DOCUMENTS

| | | |
|---|---|---|
| CN | 101105690 A | 1/2008 |
| CN | 201311715 Y | 9/2009 |
| CN | 102023599 A | 4/2011 |
| CN | 202002671 U | 10/2011 |
| CN | 102691523 A | 9/2012 |
| DE | 101 42 711 A1 | 3/2003 |
| EP | 0 0240 713 A1 | 10/1987 |

(Continued)

OTHER PUBLICATIONS

Codel International Ltd., Tunnel Atmosphere Monitoring, "TunnelCraft 3—Air Quality Monitor", Product Data Sheet, Doc I/d: 100004, Issue: A, Rev: 1, Date: Sep. 11, 2010.

(Continued)

Primary Examiner — Laura Martin
Assistant Examiner — Alex Devito
(74) Attorney, Agent, or Firm — Nath, Goldberg & Meyer; Jerald L. Meyer

(57) ABSTRACT

A tunnel monitoring sensor for monitoring environmental conditions in a tunnel comprises a first sensor module which outputs an obscuration signal, a second sensor module which outputs a first gas concentration signal, a common housing for the first and second sensor modules and an electronic logic unit which is preferably accommodated in the housing, which receives the obscuration signal and the gas concentration signal and which outputs a combined environmental condition signal on the basis of a link of the obscuration signal and of the gas concentration signal.

16 Claims, 3 Drawing Sheets

(56) References Cited

FOREIGN PATENT DOCUMENTS

EP           1521061  A2    4/2005
KR    2003 0067886  A     8/2003

OTHER PUBLICATIONS

Codel International Ltd., "TunnelCraft III—Air Quality Monitor for Visibility", Product Data Sheet.
EPO; European Search Report and English translation for corresponding European Application; Apr. 18, 2013.
Codel International Ltd., Tunnel Atmosphere Monitoring, "TunnelCraft 3—Air Quality Monitor", Product Data Sheet, Doc I/d: 100004, Issue: A, Rev: 5, Date: Feb. 11, 2011 (revised).

\* cited by examiner

TUNNEL MONITORING SENSOR

The present invention relates to a tunnel monitoring sensor for monitoring environmental conditions in a tunnel having a first sensor module which outputs an obscuration signal and having a second sensor module which outputs a first gas concentration signal.

Such sensors are usually mounted in the interior of tunnels to detect the current state of the environmental air in the tunnel. It is essential for safety reasons, in particular in road traffic tunnels and railroad traffic tunnels, to recognize specific events such as the formation of fog, smoke development, fine particulate air pollution or increased exhaust gas concentrations in good time. As a rule, the monitoring of the different measured parameters takes place using a plurality of sensors which are mounted in the tunnel and whose signals are supplied to a central control device which is located, for example, in a tunnel monitoring and control complex. The signals of all sensors present are evaluated in the control device. Measures are initiated as required with reference to the evaluation in order to react to specific disturbance events. For example, on an increase in the exhaust gas concentration, the rotational speed of the fans of a ventilation system installed in the tunnel can be increased, or in the event of smoke development, a tunnel closure can be triggered.

It is generally necessary due to applicable safety regulations to interrupt traffic in the tunnel at least in part in the case of a servicing of the sensors. This is associated with high costs for the tunnel operator as a rule. On the mounting of a new sensor or on the replacement of a defective sensor, the closure time can be extended in that a calibration of the new sensor has to be carried out on site. A further problem in the monitoring of environmental conditions in tunnels is that false alarms are often particularly expensive since they are associated with far-reaching consequences such as a tunnel closure or a longer operation of the ventilation system at an elevated rotational speed of the fans and with accordingly increased electricity costs.

It is an object of the invention to provide a tunnel monitoring sensor which is simple to mount and to service and which has an increased reliability.

The object is satisfied by a tunnel monitoring sensor having the features of claim 1.

In accordance with the invention, a tunnel monitoring sensor has a common housing for the first and second sensor modules as well as an electronic logic unit which is preferably accommodated in the housing, which receives the obscuration signal and the gas concentration signal and which outputs a combined environmental condition signal on the basis of a link of the obscuration signal and of the gas concentration signal.

At least two different sensor signals are therefore bundled and are output in the form of a common environmental condition signal. Since the two sensor modules are integrated in a common housing, the installation is facilitated with respect to an arrangement of two separate sensor modules. Since a linking of the obscuration signal and of the simultaneously provided gas concentration signal is already carried out by the tunnel monitoring sensor itself, a more differentiated evaluation can take place overall so that the risk of false alarms is reduced. Both the obscuration and the concentration of a specific gas can in particular already be taken into account on the recognition of disturbance incidents at the sensor side. For example, with a simultaneous increase in the obscuration signal and in the gas concentration signal, an environmental condition signal could be output which indicates congestion in the tunnel. The combined environmental condition signal based on such an advance evaluation can then be subjected to a furthergoing evaluation in the tunnel monitoring and control complex. It is, however, also possible to use the combined environmental condition signal directly, i.e. without a subsequent evaluation, e.g. in that a tunnel monitoring sensor in accordance with the invention is directly connected to a control device of the ventilation system. In both cases, the combined environmental condition signal allows a more effective introduction of measures against disturbance events than would be possible when using conventional individual sensors.

Further developments of the invention are set forth in the dependent claims, in the description and in the enclosed drawings.

In accordance with an embodiment of the invention, the first sensor module and the second sensor module are configured for outputting respective digital signals, with the electronic logic unit outputting a combined digital environmental condition signal on the basis of a logical connection of the digital obscuration signal and the digital gas concentration signal. A particularly reliable classification of the current environmental conditions in the tunnel can be achieved by such a logical link of at least two digital measured signals.

The logical connection can in this respect include a pattern recognition. This in particular allows a particularly exact classification of environmental conditions or of disturbance events on a presence of a plurality of sensor signals.

The electronic logic unit preferably outputs the combined digital environmental signal via a standard digital interface, in particular via PROFIBUS interface. This is in particular of advantage since only one single cable is required to transmit all desired sensor signals and the installation is particularly simple overall. The individual sensor modules of the tunnel monitoring sensor can be connected to the electronic logic unit via internal bus interfaces or via a serial interface.

In accordance with a further embodiment of the invention, a tunnel monitoring sensor comprises at least one further sensor module which outputs a further gas concentration signal, with the first gas concentration signal and the further gas concentration signal relating to different target gases and the electronic logic unit outputting the combined environmental condition signal on the basis of a link of the obscuration signal, of the first gas concentration signal and of the further gas concentration signal. Additional sensor modules for further target gases can also be provided depending on the application. It is possible in this manner to take account of the concentrations of different hazardous gases such as carbon monoxide, nitrogen monoxide and nitrogen dioxide in the evaluation of the environmental conditions in the tunnel. An identifications of the respective sensor module which can be read by the electronic logic unit can in this respect allow an unambiguous association between the respective gas concentration signal and the target gas. The tunnel monitoring sensor can thus easily be retrofitted with sensor modules for additional target gases as required.

A specific embodiment of the invention provides that the second sensor module is attached to a wall section of the housing, with a measuring head of the second sensor module passing through a leadthrough of the wall section into the outside space. The measuring head can thus directly detect the gas concentration in the environmental air of the tunnel monitoring sensor. The detection of the gas concentration by the measuring head can generally take place by means of molecular absorption of the transmitted light at a predefined wavelength, by means of an electrochemical cell or by means of a semiconductor element.

Provision can be made that the first sensor module is arranged completely within the housing, with the housing having at least one air inlet opening. The environmental air of the tunnel monitoring sensor can enter into the housing through the air inlet opening so that the first sensor module can determine the obscuration over a predefined distance e.g. using light scattering.

The first sensor module preferably comprises a scattered light sensor. Scattered light sensors are based on the detection of the light portion deflected at a specific angle to the irradiation direction of a light source and allow a reliable recognition of the current obscuration.

A further embodiment of the invention provides at least one further sensor module which outputs a temperature signal and/or a humidity signal, with the electronic logic unit outputting the combined environmental condition signal on the basis of a link of the obscuration signal, of the first gas concentration signal and additionally of the temperature signal and/or of the humidity signal. This allows the taking into account of the temperature and of the air humidity in the tunnel when evaluating the environmental conditions. For example, the electronic logic unit can output a "fog" signal on a simultaneous increase of the obscuration signal and of the humidity signal as well as on an unchanged gas concentration signal and an unchanged temperature signal. On an increase in the obscuration signal without a simultaneous increase in the gas concentration signal, in the humidity signal and in the temperature signal, the electronic logic unit can, in contrast, output a "fine particulate" signal. A semiconductor sensor which detects both the humidity and the temperature can in particular be provided as a further sensor module.

The electronic logic unit can furthermore be configured for outputting an error signal which indicates a function status of the first sensor module and/or of the second sensor module. A malfunction or a failure of one of the sensor modules can thus be recognized in good time, e.g. in the associated tunnel monitoring and control complex. This increases the security of the overall system.

A further embodiment of the invention provides that the first sensor module and/or the second sensor module comprises/comprise a memory device in which calibration parameters of the respective sensor module are stored. On a new installation or on a replacement of a sensor module, complex calibration and parameterization processes are thus superfluous since the new sensor module already provides all the required parameters.

In accordance with a further embodiment of the invention, the first sensor module and/or the second sensor module comprises/comprise a microprocessor which is in particular configured for carrying out a self-test of the respective sensor module. The sensor modules are therefore so-to-say equipped with their own intelligence so that the reliability of the tunnel monitoring sensor can be further increased.

Furthermore, at least one connector for an additional sensor module located outside the housing can be provided at the housing. Not only the sensor modules integrated into the housing, but, if required, separate sensor modules can thus also be evaluated in order thus to generate a further differentiated combined environmental condition signal.

The invention also relates to a tunnel monitoring method for monitoring environmental conditions in a tunnel, wherein an obscuration signal is generated by means of a first sensor module arranged in a housing, a first gas concentration signal is generated by means of a second sensor module arranged in the housing, the obscuration signal and the gas concentration signal are linked together and a combined environmental condition signal is generated on the basis of the link.

Advantages and preferred embodiments of a tunnel monitoring method in accordance with the invention result from the aforesaid advantages and preferred embodiments of a tunnel monitoring sensor in accordance with the invention.

The invention will be described in the following by way of example with reference to the drawings.

Figure 1:
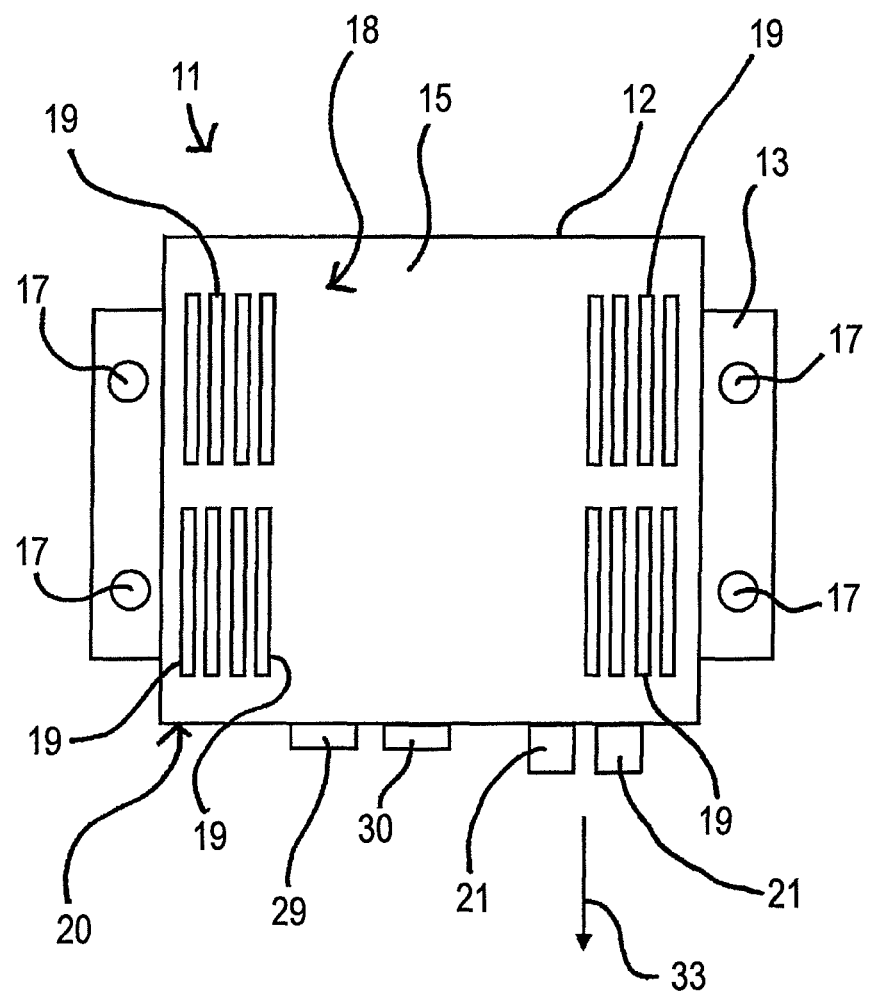
FIG. 1 is a plan view of a tunnel monitoring sensor in accordance with a first embodiment of the invention.

The tunnel monitoring sensor 11 shown in FIG. 1 serves for the monitoring of environmental conditions in a road traffic tunnel or rail traffic tunnel and has a housing 12 which has a support part 13 and also a half-shell-like cover 15. Fastening openings 17 are provided at the carried part 13 which serve for the attachment of the tunnel monitoring sensor 11 in the tunnel, for example by means of screws. The cover 15 is removable from the support part 13 for servicing purposes. A plurality of arrangements of air inlet openings 19 are provided at the upper side 18 of the housing 12. The housing 12 moreover has two electrical connectors 21 at an end face 20 for connecting the tunnel monitoring sensor 11 to a downstream arrangement of a monitoring system and also for the power supply.

Figure 2:
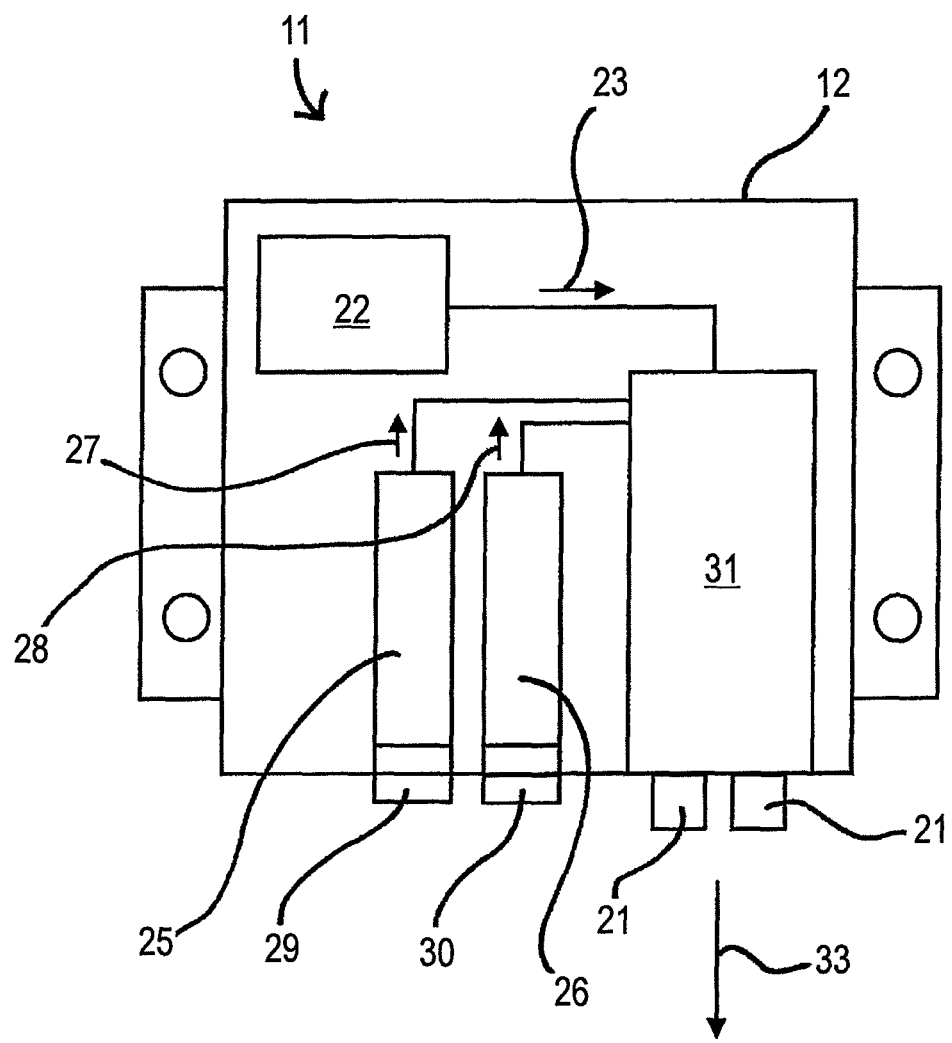
FIG. 2 shows the tunnel monitoring sensor in accordance with FIG. 1 in a partly cut-away representation.

As can be seen from the cut-away representation in accordance with FIG. 2, the tunnel monitoring sensor 11 has a scattered light sensor module 22 which is acted on by the environment air entering through the air inlet openings 19 into the housing 12 and preferably outputs a digital obscuration signal 23. Furthermore, two gas concentration sensor modules 25, 26 are attached within the housing 12 such that their measuring heads 29, 30 extend through leadthroughs of the housing 12 which are not shown separately into the outside space of the tunnel monitoring sensor 11. The gas concentration sensor modules 25, 26 have electronic processing devices, not shown, including corresponding microprocessors and memory devices and output respective gas concentration signals, preferably digital gas concentration signals 27, 28. In this respect, the two gas concentration signals 27, 28 relate to different target gases, for example to carbon monoxide, on the one hand, and to nitrogen monoxide, on the other hand.

An electronic logic unit 31 is also accommodated in the housing 12 and receives both the obscuration signal 23 and the two gas concentration signals 27, 28. The electronic logic unit 31 is configured to generate a combined environmental condition signal 33 on the basis of a logical connection of the obscuration signal 23 and of the two gas concentration signals 27, 28 and to output it via the electrical connectors 21. The electronic logic unit 31 preferably outputs the combined environmental condition signal 33 via a standard digital interface such as the PROFIBUS interface. The communication of the scattered light sensor module 22 and of the gas concentration sensor modules 25, 26 with the electronic logic unit 31 preferably also takes place via digital interfaces.

Depending on the application, the logical connection of the obscuration signal 23 and of the gas concentration signals 27, 28 can be relatively simple, i.e. be based, for example, on a sum formation and/or difference formation, or a complex processing of the input signals can take place, for example using a pattern recognition algorithm.

Depending on the application, further sensor modules can also be arranged in the housing 12, e.g. further gas concentration sensor modules for other target gases, a humidity sensor and/or a temperature sensor. In accordance with an embodiment, not shown, the housing 12 additionally has an input connector for connecting an additional external sensor to the tunnel monitoring sensor 11.

During the operation of the tunnel monitoring sensor 11, the electronic logic unit 31 links the obscuration signal 23 to the two gas concentration signals 27, 28 and outputs a report, in the form of the combined environmental condition signal 33, on the current state in the tunnel including possible disturbances and hazards. For example, the combined environmental condition signal 33 can indicate the presence of fog or of a fine particulate pollution on an increase in the obscuration signal 23 without a simultaneous increase in the gas concentration signals 27, 28. Provided a humidity sensor is additionally installed, a distinction can further be made on the basis of the increase in the humidity signal between the presence of fog and fine particulate pollution. Provided a temperature sensor is additionally installed, the combined environmental condition signal 33 can e.g. indicate a risk of explosion when the gas concentration signals 27, 28 reach critical values, but an increase in the humidity signal and in the temperature signal does not take place. The combined environmental condition signal 33 could equally indicate a hazardous atmosphere on the reaching of a toxic gas concentration. On a fast increase in the obscuration signal 23 and simultaneously in the gas concentration signals 27, 28 as well as, optionally, in a temperature signal, the combined environmental condition signal 33 can indicate a fire. An increase in the obscuration signal 23 and in the gas concentration signals 27, 28 without a simultaneous increase in the humidity signal and in the temperature signal can, in contrast, indicate congestion.

A central control device in the tunnel monitoring and control complex can read out the combined environmental condition signal 33 via the PROFIBUS interface, can, if necessary, put them into relation with further combined environmental condition signals 33 from other tunnel monitoring sensors 11 and can initiate corresponding measures on a recognition of disturbances. For example, an intervention can be made in the control of the ventilation system. A fire alarm and a tunnel closure can equally be triggered on a finding of a fire.

In the previously described embodiment, the logic unit 31 optionally also provides an evaluation of the raw signals before the link—for example a digitizing. This function can, however, also be implemented in a separate evaluation unit.

Figure 3:
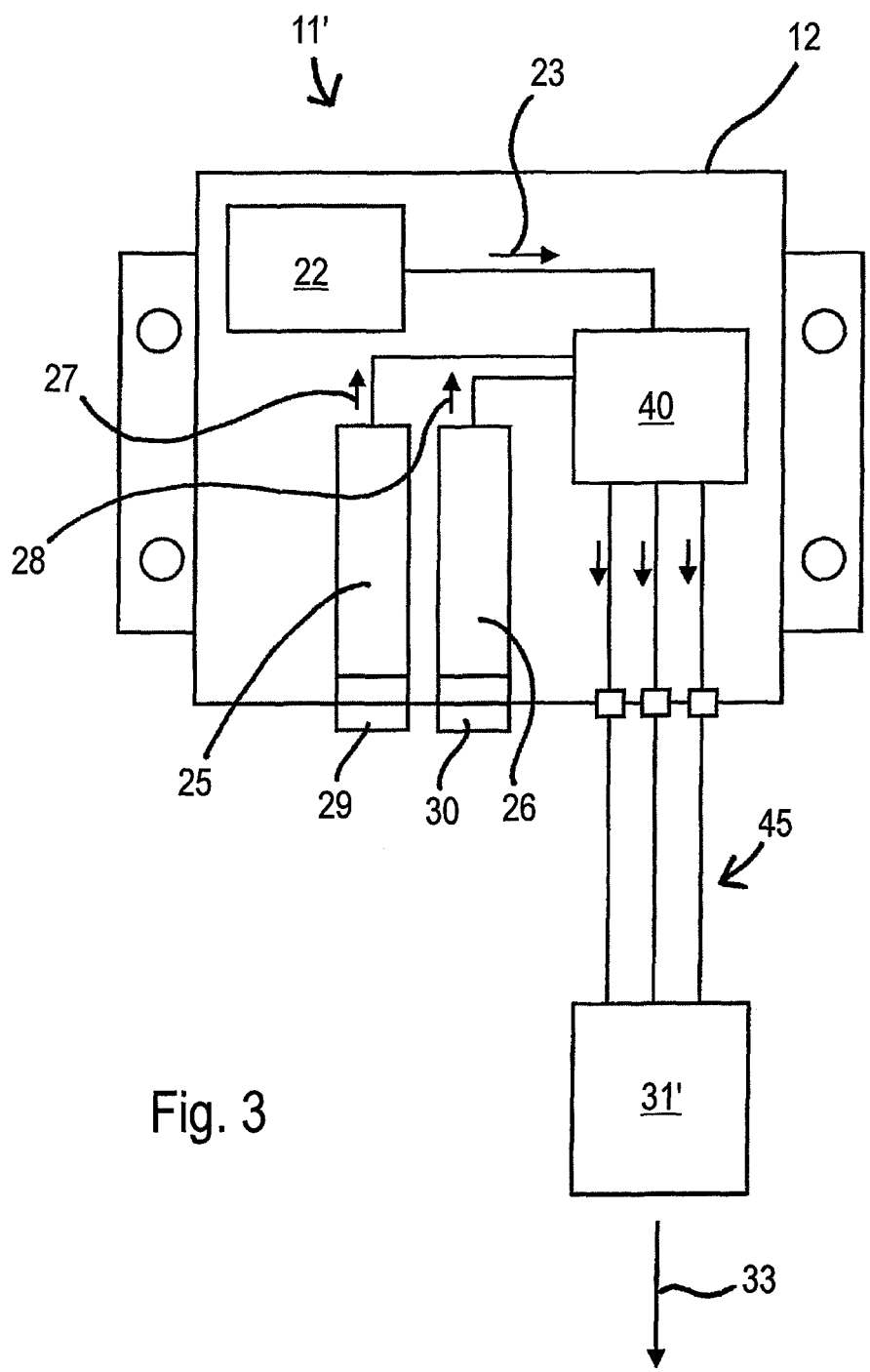
FIG. 3 shows a tunnel monitoring sensor in accordance with a second embodiment of the invention in a partly cut-away representation.

FIG. 3 shows an alternative embodiment of a tunnel monitoring sensor 11' in accordance with the invention which has a similar design to the tunnel monitoring sensor 11 shown in FIGS. 1 and 2, but with the electronic logic unit 31' being configured in a higher-ranking control located outside the housing 12. This external logic unit 31' can in particular be a programmable logic control (PLC). Furthermore, an electronic evaluation unit 40 which is arranged in the housing 12 in this embodiment is provided in the tunnel monitoring sensor 11' shown in FIG. 3. The electronic evaluation unit 40 receives the obscuration signal 23 as well as the two gas concentration signals 27, 28 and prepares them in that it e.g. digitizes them provided that the signals are not already present in digital form. In principle, a separate evaluation unit could also be provided for each of the raw signals present. The obscuration signal 23 and the two gas concentration signals 27, 28 are then transmitted in prepared form via a transfer path 45 to the external logic unit 31'. This then carries out a link as above with reference to FIGS. 1 and 2 and outputs the combined environmental signal 33 on the basis of the link.

Since the tunnel monitoring sensor 11, 11' outputs a combined environmental condition signal 33 in which a plurality of different measured parameters, which are, however, detected simultaneously, are processed, a particularly reliable classification of the current state is possible. False alarms can in particular be avoided. The installation of the tunnel monitoring sensor 11 is simplified by the integration of a plurality of different sensor modules into a common housing 12. In addition, the system can be simply expanded and provided with additional sensor elements on site without changing the existing cabling between the sensor and the tunnel monitoring and control complex. Since calibration parameters are stored in corresponding electronic memory devices in the individual sensor modules 22, 25, 26, the complex calibration of the sensor modules 22, 25, 26 on site as part of a new installation is dispensed with. In addition, due to a self-test function, the failure of a sensor module 22, 25, 26 or of the total tunnel monitoring sensor 11, 11' can be recognized at an early time.

REFERENCE NUMERAL LIST 11, 11' tunnel monitoring sensor
12 housing
13 support part
15 cover
17 fastening opening
18 upper side
19 air inlet opening
20 end face
21 electrical connector
22 scattered light sensor module
23 obscuration signal
25 gas concentration sensor module
26 gas concentration sensor module
27 gas concentration signal
28 gas concentration signal
29 measuring head
30 measuring head
31, 31' electronic logic unit
33 combined environmental condition signal
40 electronic evaluation unit
45 transmission path

The invention claimed is:

1. A tunnel monitoring sensor (11, 11') for monitoring environmental conditions in a tunnel comprising:
    a first sensor module (22) which outputs an obscuration signal (23);
    a second sensor module (25) which outputs a first gas concentration signal (27);
    a common housing (12) for the first and second sensor modules (22, 25); and
    an electronic logic unit (31, 31') which receives the obscuration signal (23) and the gas concentration signal (27) and which outputs a combined environmental condition signal (33) on the basis of a link of the obscuration signal (23) and the gas concentration signal (27), wherein the combined environmental condition signal represents a report on the current state in the tunnel, including possible disturbances and hazards; and wherein the first sensor module (22) comprises a scattered light sensor and is arranged completely within the housing (12), with the housing (12) having at least one air inlet opening (19).

2. The tunnel monitoring sensor in accordance with claim 1, wherein the electronic logic unit (31, 31') is accommodated in the housing (12).

3. The tunnel monitoring sensor in accordance with claim 1, wherein the first sensor module (22) and the second sensor module (25) are configured for outputting respective digital signals (23, 27), with the electronic logic unit (31, 31') outputting a combined digital environmental condition signal (33) on the basis of a logical connection of the digital obscuration signal (23) and of the digital gas concentration signal (27).

4. The tunnel monitoring sensor in accordance with claim 3, wherein the logical connection includes a pattern recognition.

5. The tunnel monitoring sensor in accordance with claim 3, wherein the electronic logic unit (31, 31') outputs the combined digital environmental condition signal (33) via a standard digital interface.

6. The tunnel monitoring sensor in accordance with claim 5, wherein the electronic logic unit (31, 31') outputs the combined digital environmental condition signal (33) via a PROFIBUS interface.

7. The tunnel monitoring sensor in accordance with claim 1, further comprising at least one further sensor module (26) which outputs a further gas concentration signal (28), with the first gas concentration signal (27) and the further gas concentration signal (28) relating to different target gases and the electronic logic unit (31, 31') outputting the combined environmental condition signal (33) on the basis of a link of the obscuration signal (23), of the first gas concentration signal (27) and of the further gas concentration signal (28).

8. The tunnel monitoring sensor in accordance with claim 1, wherein the second sensor module (25) is attached to a wall section of the housing (12), with a measuring head (29) of the second sensor module (25) extending into the outside space through a leadthrough of the wall section.

9. The tunnel monitoring sensor in accordance with claim 1, further comprising at least one further sensor module which outputs a temperature signal and/or a humidity signal, with the electronic logic unit (31, 31') outputting the combined environmental condition signal (33) on the basis of a link of the obscuration signal (23), of the first gas concentration signal (27) and additionally of the temperature signal and/or of the humidity signal.

10. The tunnel monitoring sensor in accordance with claim 1, wherein the electronic logic unit (31, 31') is configured for outputting an error signal which indicates a functional status of the first sensor module (22) and/or of the second sensor module (25).

11. The tunnel monitoring sensor in accordance with claim 1, wherein the first sensor module (22) and/or the second sensor module (25) comprises/comprise a memory device in which calibration parameters of the respective sensor module (22, 25) are stored.

12. The tunnel monitoring sensor in accordance with claim 1, wherein the first sensor module (22) and/or the second sensor module (25) comprises/comprise a microprocessor.

13. The tunnel monitoring sensor in accordance with claim 12, wherein the microprocessor(s) is/are configured for carrying out a self-test of the respective sensor module (22, 25).

14. The tunnel monitoring sensor in accordance with claim 1, wherein at least one connector for an additional sensor module located outside the housing (12) is provided at the housing (12).

15. A tunnel monitoring method for monitoring environmental conditions in a tunnel, comprising the steps of:

generating an obscuration signal (23) by means of a first sensor module (22) arranged in a housing (12);

generating a first gas concentration signal (27) by means of a second sensor module (25) arranged in the housing (12);

linking the obscuration signal (23) and the gas concentration signal (27) to one another; and generating a combined environmental condition signal (33) on the basis of the link, wherein the combined environmental condition signal represents a report on the current state in the tunnel, including possible disturbances and hazards; and wherein the first sensor module (22) comprises a scattered light sensor and is arranged completely within the housing (12), with the housing (12) having at least one air inlet opening (19).

16. A tunnel monitoring sensor (11, 11') for monitoring environmental conditions in a tunnel comprising:

a first sensor module (22) which outputs an obscuration signal (23);

a second sensor module (25) which outputs a first gas concentration signal (27);

a common housing (12) for enclosing the first and second sensor modules (22, 25), said housing (12) including at least one air inlet opening (19); and an electronic logic unit (31, 31') which receives the obscuration signal (23) and the gas concentration signal (27) and which outputs a combined environmental condition signal (33) on the basis of a link of the obscuration signal (23) and the gas concentration signal (27), wherein the first sensor module (22) comprises a scattered light sensor and is arranged completely within the housing (12), and wherein the combined environmental condition signal represents a report on the current state in the tunnel, including possible disturbances and hazards.

* * * * *